United States Patent [19]

Wootton et al.

[11] 4,315,022
[45] Feb. 9, 1982

[54] TERMINAL AMINO PROSTAGLANDIN ANALOGUES

[75] Inventors: Gordon Wootton, Sawbridgeworth; Stephen A. Smith, Harlow, both of England

[73] Assignee: Beecham Group Limited, England

[21] Appl. No.: 152,766

[22] Filed: May 23, 1980

[30] Foreign Application Priority Data

May 23, 1979 [GB] United Kingdom ............... 17931/79

[51] Int. Cl.³ .................. A61K 31/415; C07D 233/78; C07D 233/86; C07D 233/32
[52] U.S. Cl. .......................... 424/273 R; 260/465 D; 260/465.4; 548/301; 548/313; 560/168; 560/169
[58] Field of Search ............... 548/301, 313; 424/273 R

[56] References Cited

U.S. PATENT DOCUMENTS

| | | | |
|---|---|---|---|
| 4,147,796 | 4/1979 | Wootton | 548/313 X |
| 4,152,445 | 5/1979 | Wootton | 548/313 X |
| 4,204,068 | 5/1980 | Caldwell et al. | 548/313 |

OTHER PUBLICATIONS

House, M., Modern Synthetic Reactions, W. A. Benjamin, New York, 1965, pp. 34 and 36.
Chemical Abstracts, 92: 181,185g, (1980), [German Ols 2,922,070, Caldwell et al., 12/6/79].

Primary Examiner—Richard A. Schwartz
Attorney, Agent, or Firm—Jacobs & Jacobs

[57] ABSTRACT

Compounds of the formula (I):

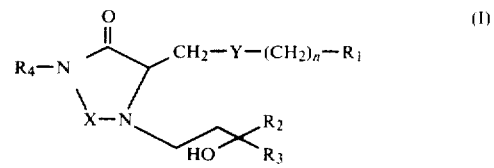

having pharmacological activities similar to those of natural prostaglandins wherein:

n is 0 to 5;

X is CO, CS or $CH_2$;

Y is $-CH_2-CH_2-$; or, when n is 1 to 5, $-CH=CH-$ or $-C\equiv C-$;

$R_1$ is either $CH_2NR_5R_6$, wherein $R_5$ and $R_6$ are separately hydrogen or $C_{1-6}$ alkyl, or $R_5$ is hydrogen and $R_6$ is $(CH_2)_mCO_2R^1{}_9$ wherein m is 0 to 4 and $R^1{}_9$ is optionally substituted $C_{1-6}$ alkyl or benzyl, optionally substituted in the phenyl ring by chlorine or bromine atoms or by nitro or $CF_3$ groups; or $R_5$ and $R_6$ are both the same $(CH_2)_mCO_2R^1{}_9$ as hereinbefore defined; or $C(NH_2)=NOH$; or $C(OR_7)=NH_2{}^+B^-$ wherein $R_7$ is $C_{1-6}$ alkyl and $B^-$ is a salting ion; or $CH_2NHR_8$, wherein $R_8$ is $SO_2R^1{}_9$, $COR^1{}_9$ or $CZNHR_9$ and $R^1{}_9$ is as hereinbefore defined, $R_9$ is hydrogen or $C_{1-6}$ alkyl and Z is oxygen or sulphur; or $CZNH_2$ wherein Z is as hereinbefore defined:

$R_2$ is hydrogen or $C_{1-4}$ alkyl;

$R_3$ is $C_{1-9}$ alkyl, $C_{5-8}$ cycloalkyl or $C_{5-8}$ cycloalkyl $-C_{1-6}$ alkyl; or $R_2$ and $R_3$ taken with the carbon atom to which they are joined represent a $C_{5-8}$ cycloalkyl group; and $R_4$ is hydrogen or $C_{1-6}$ alkyl; and salts thereof; with the provisos (i) that when X is $CH_2$ then Y must be $-CH_2-CH_2-$, and (ii) when $R_1$ is $CH_2NR_5R_6$ or $CH_2NHR_8$ then Y must be $-CH_2-CH_2-$, pharmaceutical compositions containing them and processes for their preparation.

34 Claims, No Drawings

TERMINAL AMINO PROSTAGLANDIN ANALOGUES

This invention relates to novel compounds having pharmacological activity, to a process for their preparation, to intermediates useful in that process and to pharmaceutical compositions containing them.

W. German Offenlegungsschrift No. 2724948 discloses that compounds of the general formula (A):

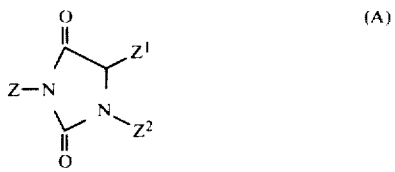

wherein

Z is hydrogen or alkyl; one of $Z^1$ and $Z^2$ is a group $-CH_2-X-X^1-X^2$ in which X is phenylene, $-C\equiv C-$, cis- or trans $-CH=CH-$ or $-CH_2-CQ_2-$ where each radical Q independently of the other is hydrogen and or alkyl or the two radicals Q together are $C_{4-6}$ alkylene; $X^1$ is a covalent bond or a straight or branched $C_{1-6}$ alkylene chain, in which one methylene group is optionally substituted by an oxa ($-O-$) group, with the proviso that at least one carbon atom separates the oxa group from a $-C\equiv C-$, $-CH=CH-$ or $-CO-$ group; and $X^2$ is 5 tetrazolyl, carboxyl, carboxamide, hydroxymethylene alkoxycarbonyl; and the other one of $Z^1$ and $Z^2$ is a group $-Y-Y^1-Y^2-Y^3$ in which Y is $-CR_2-CH_2-$, where each radical R independently of the other is hydrogen or methyl; $Y^1$ is carbonyl, methylene, methylene substituted by a hydroxy group or methylene substituted by a hydroxy and alkyl group; $Y^2$ is a covalent bond or straight-chain or branched $C_{1-7}$ alkylene optionally substituted on the carbon atom adjacent to $Y^1$ by one or two mutually independent alkyl, bicycloalkyl or cycloalkyl groups;

$Y^3$ is hydrogen, hydroxy, $C_{1-7}$ (preferably $C_{1-4}$) alkoxy, cycloalkyl, bicycloalkyl, phenyl, benzyl, phenoxy or benzyloxy, where each phenyl, benzyl, phenoxy or benzyloxy group may be substituted in the benzene ring by one or more hydroxy, halogen, nitro, amino, acylamino, alkenyl, alkoxy, phenyl or alkyl groups, which alkyl may itself be substituted by one or more halogens; or Y is a bond, $-CH_2-$ or $-CH_2.CH_2-$ and $Y^1$, $Y^2$ and $Y^3$ together are cycloalkyl which is substituted by a hydroxy group which is preferably separated by 3 carbon atoms from the hydantoin ring; have similar pharmacological activity to natural prostaglandins.

Our W. German Offenlegungsschrift No. 2755771 discloses compounds of formula (B):

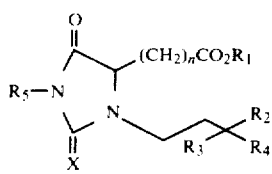

wherein:

X is O to S;

n is 1 to 8;

$R_1$ is hydrogen, or $CO_2R_1$ represents an ester group in which the $R_1$ moiety contains from 1-12 carbon atoms;

$R_2$ is hydrogen, $C_{1-4}$ alkyl, or phenyl;

$R_3$ is hydroxy or protected hydroxy;

$R_4$ is hydrogen, $C_{1-9}$ alkyl, $C_{3-8}$ cycloalkyl, $C_{3-8}$ cycloalkyl-$C_{1-6}$ alkyl, phenyl, phenyl $C_{1-6}$ alkyl, naphthyl, naphthyl-$C_{1-6}$ alkyl, any of which phenyl or naphthyl moieties may be substituted by one or more halogen, trifluoromethyl, $C_{1-6}$ alkyl, hydroxy, $C_{1-6}$ alkoxy, phenyl $C_{1-6}$ alkoxy or nitro groups; or $R_2$ and $R_4$ taken with the carbon atom to which they are joined represent a $C_{5-8}$ cycloalkyl group;

$R_5$ is hydrogen, $C_{1-6}$ alkyl, $C_{1-6}$ alkyl substituted by a nitro, hydroxy, $C_{1-6}$ alkoxy, $CO_2A$, $(CO_2A)_2$, CN or halogen group, $C_{5-8}$ cycloalkyl, phenyl, phenyl-$C_{1-6}$ alkyl, phenyl-$C_{3-6}$ cycloalkyl, any of which phenyl moieties may be substituted by one or more halogen, trifluoromethyl, $C_{1-6}$ alkyl, $C_{1-6}$ alkoxy or nitro groups; or a group $CO_2A$; in $R_5$ when present A is hydrogen or $CO_2A$ represents an ester group in which the A moiety contains from 1 to 12 carbon atoms; and salts thereof; as having useful prostaglandin-like activity.

We have now discovered a class of compounds which have useful pharmacological activity. This class is structurally distinct from the compounds described in the aforementioned Offenlegungsschrifts, with the exception of a narrow group of compounds which although falling within the broad general disclosure of Offenlegungsschrift No. 2724948, is not in any way specifically described therein.

Accordingly the present invention provides a compound of the formula (I):

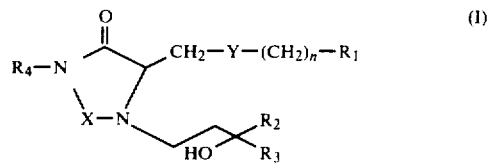

wherein:

n is 0 to 5;

X is CO, CS or $CH_2$;

Y is $-CH_2-CH_2-$; or, when n is 1 to 5, $-CH=CH-$ or $-C\equiv C-$;

$R_1$ is either $CH_2NR_5R_6$, wherein $R_5$ and $R_6$ are separately hydrogen or $C_{1-6}$ alkyl, or $R_5$ is hydrogen and $R_6$ is $(CH_2)_mCO_2R^1{}_9$ wherein m is 0 to 4 and $R^1{}_9$ is optionally substituted $C_{1-6}$ alkyl or benzyl, optionally substituted in the phenyl ring by chlorine or bromine atoms or by nitro or $CF_3$ groups; or $R_5$ and $R_6$ are both the same $(CH_2)_mCO_2R^1{}_9$ as hereinbefore defined; or $C(NH_2)=NOH$; or $C(OR_7)=NH_2{}^+B^-$ wherein $R_7$ is $C_{1-6}$ alkyl and $B^-$ is a salting ion; or $CH_2NHR_8$, wherein $R_8$ is $SO_2R^1{}_9$, $COR^1{}_9$ or $CZNHR_9$ and $R^1{}_9$ is as hereinbefore defined, $R_9$ is hydrogen or $C_{1-6}$ alkyl and Z is oxygen or sulphur; or $CZNH_2$ wherein Z is as hereinbefore defined;

$R_2$ is hydrogen or $C_{1-4}$ alkyl;

$R_3$ is $C_{1-9}$ alkyl, $C_{5-8}$ cycloalkyl or $C_{5-8}$ cycloalkyl-$C_{1-6}$ alkyl; or $R_2$ and $R_3$ taken with the carbon atom to which they are joined represent a $C_{5-8}$ cycloalkyl group; and $R_4$ is hydrogen or $C_{1-6}$ alkyl; and salts thereof; with the provisos (i) that when X is $CH_2$ then Y must be —$CH_2$—$CH_2$—, and (ii) when $R_1$ is $CH_2NR_5R_6$ or $CH_2NHR_8$ then Y must be —$CH_2$—$CH_2$—.

Often n is 2 to 4, for example 3.

Most suitably X is CO or CS, preferably CO.

Suitably Y may be —$CH_2$—$CH_2$— or —CH=CH, preferably —$CH_2$—$CH_2$—.

Suitable examples of $R_1$ when it is a group of formula $CH_2NR_5R_6$ include $CH_2NH_2$, $CH_2NHCH_3$, $CH_2N(CH_3)_2$, $CH_2NHC_2H_5$, $CH_2N(C_2H_5)_2$, and also $CH_2NH(CH_2)_mCO_2R^1_9$ and $CH_2N[(CH_2)_mCO_2R^1_9]_2$ wherein suitably $R^1_9$ is methyl or ethyl. When $R_1$ contains the $(CH_2)_mCO_2R^1_9$ moiety then n + m in the resultant compound of the formula (I) is suitably 0 to 2. When $R^1_9$ is $C_{1-6}$ alkyl, n + m is preferably 1. When $R^1_9$ is optionally substituted $C_{1-6}$ alkyl or benzyl as hereinbefore defined n + m is preferably 0. Suitably substituted $C_{1-6}$ alkyl includes 2-sulphonyl substituted ethyl. Preferred $R_1$ groups of the $CH_2NR_5R_6$ type include $CH_2NH_2$.

Suitable examples of $R_1$ groups $C(OR_7)=NH_2{}^+B^-$ are those wherein $R_7$ is hydrogen, methyl or ethyl, and $B^-$ is a halide such as chloride. One particular example of such a group is $C(OCH_3)=NH_2{}^+Cl^-$.

When $R_1$ is $CH_2NHR_8$, and contains a $R_9$ or $R^1_9$ group, then $R_9$ or $R^1_9$ is suitably (hydrogen), methyl, ethyl, n- and iso-propyl, and n-, sec- and tert-butyl.

Thus examples of $R_1$ $CH_2NHR_8$ groups include $CH_2NHSO_2CH_3$, $CH_2NHCOCH_3$, $CH_2NHCONH_2$, $CH_2NHCONHCH_3$, $CH_2NHCSNH_2$, $CH_2NHCSNHCH_3$, and the like.

Suitable examples of $R_2$ include hydrogen, methyl and ethyl. More suitably $R_2$ is hydrogen or methyl, preferably methyl.

Suitable groups $R_3$ when $R_3$ is an alkyl group include $C_{4-9}$ alkyl groups. Such $C_{4-9}$ alkyl groups may be straight chain alkyl groups, such as n-butyl, n-pentyl, n-hexyl and n-heptyl, or may be alkyl groups branched by one or two methyl groups (at the same or different carbon atoms). Thus for example, $R_3$ may be a group $CH_2R_{10}$, $CH(CH_3)R_{10}$ or $C(CH_3)_2R_{10}$, wherein $R_{10}$ is straight chain alkyl group such that the carbon content of the resultant group $R_{10}$ is 4 to 9.

In general preferred groups $R_3$ when $R_3$ is an alkyl group include straight chain pentyl, hexyl and heptyl groups. Of these, straight chain hexyl is often the most useful. Other preferred groups $R_3$ include groups $CH(CH_3)R_{10}$ and $C(CH_3)_2R_{10}$ wherein $R_{10}$ is straight chain butyl, pentyl or hexyl.

Other suitable examples of $R_3$ when $R_3$ is an alkyl group include the lower alkyl groups, that is when $R_3$ is a $C_{1-4}$ alkyl group.

When $R_3$ is or contains a $C_{5-8}$ cycloalkyl, moiety, the moiety may be a cyclohexyl moiety. Examples of suitable $C_{1-6}$ alkyl moieties when $R_3$ is a $C_{5-8}$ cycloalkyl-$C_{1-6}$ alkyl group include methyl, ethyl, propyl, butyl, and pentyl.

Also, $R_2$ and $R_3$ taken with the carbon atom to which they are joined can represent a $C_{5-8}$ cycloalkyl group, such as the cyclohexyl group.

Suitable examples of $R_4$ include hydrogen, methyl, ethyl, n- and iso-propyl, n-, sec- and tert-butyl. More suitably $R_4$ is hydrogen or methyl, preferably methyl.

The compounds of the formula (I) may form conventional salts. The nature of these salts of course depends on whether the particular compound of the formula (I) contains acidic or basic groups.

In the former case the compound can form salts with alkali and alkaline earth metals, suitably sodium and potassium, and ammonium and substituted ammonium salts.

In the latter case the compound can form acid addition salts with acids, such as preferably the conventional pharmaceutically acceptable acids, for example hydrochloric, hydrobromic, phosphoric, acetic, fumaric, salicylic, citric, lactic, mandelic, tartaric and methanesulphonic acids.

It will of course be realised that the compounds of the formula (I) have asymmetric centres, and thus are capable of existing in a number of stereoisomeric forms. The invention extends to each of these stereisomeric forms, and to mixtures thereof. The different stereisomeric forms may be separated one from the other by the usual methods.

A group of compounds within formula (I) are those wherein $R_1$ is either $CH_2NR_5R_6$, wherein $R_5$ and $R_6$ are separately hydrogen or $C_{1-6}$ alkyl, or $R_5$ is hydrogen and $R_6$ is $(CH_2)_mCO_2R^1_9$ wherein m is 0 to 4 and $R^1_9$ is $C_{1-6}$ alkyl, or $R_5$ and $R_6$ are both the same $(CH_2)_mCO_2R^1_9$ as hereinbefore defined; or $C(NH_2)=NOH$; or $C(OR_7)=NH_2{}^+B^-$ wherein $R_7$ is $C_{1-6}$ alkyl and $B^-$ is a salting ion; or $CH_2NHR_8$, wherein $R_8$ is $SO_2R^1_9$, $COR^1_9$ or $CZNHR_9$ and $R^1_9$ is as hereinbefore defined, $R_9$ is hydrogen or $C_{1-6}$ alkyl and Z is oxygen or sulphur; or $CZNH_2$ wherein Z is as hereinbefore defined; and the other variables are as hereinbefore defined.

The class of compounds of the formula (I) wherein $R_1$ is $CH_2NR_5R_6$; $C(NH_2)=NOH$; $C(OR_7)=NH_2{}^+B^-$; or $CH_2NHR_8$ is of particular importance, as such compounds fall totally outside any disclosure in German Offenlegungsschrift No. 2724948.

One sub-group of compounds of the formula (I) of interest is of formula (I)$^1$:

$$\text{(I)}^1$$

wherein X' is CO or CS, and the remaining variables are as hereinbefore defined.

In this sub-group suitable and preferred examples of the variable groups therein are as hereinbefore described. X' is preferably CO. n is suitably 2 to 4, for example 3, when $R_5$ and $R_6$ are hydrogen or alkyl.

In this sub group when $R_3$ is $C_{1-9}$ alkyl then suitable and preferred straight chain and branched groups $R_3$ include those previously described as suitable and preferred for the group $R_3$ when $R_3$ is a $C_{4-9}$ alkyl group. Such preferred groups $R_3$ include straight chain pentyl, hexyl, and heptyl, and of these normally the most useful is straight chain hexyl. Other preferred groups $R_3$ include $CH(CH_3)R^1_3$ and $C(CH_3)_2R^1_3$ wherein $R^1_3$ is straight chain butyl, pentyl or hexyl.

When $R_3$ is cycloalkyl or cycloalkyl alkyl, it may be represented by formula (I)$^2$:

$$\text{(I)}^2$$

wherein:

T is a bond, or a $C_{1-6}$ alkylene group which may be straight chain or branched by one or two methyl groups at the same or different carbon atoms; and r is 0 to 3.

In formula $(I)^2$ often T will be a group —$(CH_2)_q$— wherein q is 0 to 4. Also suitably r may be 1.

When $R_2$ and $R_3$ taken with the carbon atom to which they are joined represent a $C_{5-8}$ cycloalkyl group, then this moiety of the compounds of the formula $(I)^1$ may be represented by formula $(I)^3$:

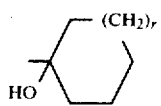

(I)³ wherein r is 0 to 3, preferably 1.

A second sub-group within formula (I) is of formula $(I)^4$:

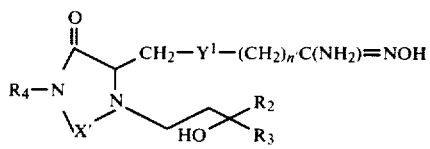

(I)⁴ wherein the variable groups are as hereinbefore defined, and their suitable and preferred values, are as hereinbefore described; Y' is —$CH_2$—$CH_2$— or —$CH=CH$—, preferably —$CH_2$—$CH_2$—, and n' is 2 to 4, preferably 3.

A third sub-group within formula (I) is of formula $(I)^5$:

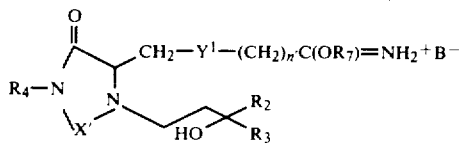

(I)⁵ wherein the variable groups are as hereinbefore defined, and their suitable and preferred values are as hereinbefore described.

A fourth sub-group within formula (I) is of formula $(I)^6$:

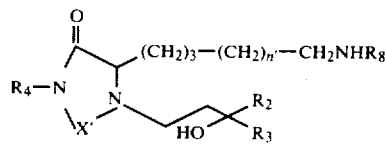

(I)⁶ wherein the variable groups are as hereinbefore defined, and suitable and preferred values are as hereinbefore described.

A fifth sub-group within formula (I) is of formula $(I)^7$:

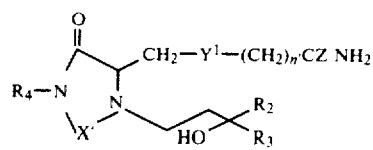

(I)⁷ wherein the variable groups, and their suitable and preferred values, are as hereinbefore described.

The invention also provides a process for the preparation of the compounds of the formula (I), which process comprises (i) reacting a compound of the formula (II):

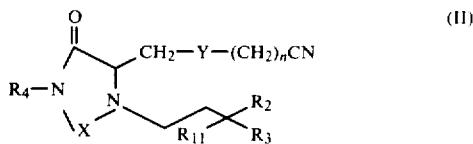

(II)

wherein $R_{11}$ is hydroxy or protected hydroxy and the other variables are as defined except that X and Y may take their full range of values with a reducing agent, to give the corresponding compound wherein Y is —$CH_2$—$CH_2$— and $R_1$ is $CH_2NH_2$, and thereafter if desired functionalising this $R_1$ group into another $R_1$ group of formula $CH_2NR_5R_6$ or $CH_2NHR_8$; or (ii) functionalising the CN group in formula (II) to give the corresponding compound of the formula (I) wherein $R_1$ is $C(NH_2)=NOH$, $C(OR_7)=NH_2{}^+B^-$, or $CZNH_2$;

and thereafter if desired or necessary converting one group X, Y or $R_4$ into another group X, Y or $R_4$, or deprotecting a protected $R_{11}$ hydroxy group.

Reduction of the CN group in the compound of formula (II) may be effected in conventional manner for such reactions, for example using hydrogen chloride and a platinium dioxide catalyst.

Conversion of a compound of formula (I) wherein $R_1$ is $CH_2NH_2$ into the corresponding compound wherein the amino function is alkylated can be carried out in any suitable manner, for example by reaction with an alkyl halide such as methyl iodide or with a group D-$(CH_2)_mCO_2R_9$ wherein D is a good leaving group. Mono- or di-alkylation can be effected as desired by control of the reaction conditions in the usual way.

Conversion of compound of the formula (I) wherein $R_1$ is $CH_2NH_2$ into the corresponding compound wherein the amino function is acylated can also be carried out in conventional manner, for example by reaction with an acid chloride of an acid of formula $HO_3S$—$R_9$ or $HO_2C$—$R_9$ under the usual acylating conditions.

Urea and thiourea derivatives of $R_1CH_2NH_2$ compounds can be prepared by reaction with $R^1{}_9NCZ$, wherein $R^1{}_9$ is as defined, or with $M^+CNZ^-$ in aqueous acid such as HCl, wherein $M^+$ is a metal ion such as an alkali metal ion, for example potassium.

Compounds of the formula (I) wherein $R_1$ is $C(NH_2)=NOH$ may be prepared by reacting the corresponding compound of the formula (II) with hydroxylamine, suitably in an alcohol such as ethanol.

Compounds of the formula (I) wherein $R_1$ is $C(OR_7)=NH_2{}^+B^-$ can be prepared by reacting the corresponding compound of the formula (II) with an alcohol and an acid, for example alcoholic HCl.

Compounds of the formula (I) wherein $R_1$ is $CZNH_2$ may be prepared by reaction of the corresponding compound of the formula (II) with $H_2O_2$ in aqueous acetone at room temperature to give the Z is oxygen compound, and with $H_2S$ and a tertiary amine to give the Z is sulphur compound. The thio compound can also be prepared by reaction of the compound of formula (II) with thioacetamide in dimethylformamide saturated with hydrogen chloride.

Compounds of formula (I) wherein X is $CH_2$ may be prepared from the corresponding compound wherein X is CS by reduction.

This reductive desulphurisation may be carried out in the presence of a suitable conventional hydrogenation catalyst, such as Raney nickel, under conventional conditions, for such reactions. For example a solution of the chosen compound of the formula (II) in an organic solvent may be added to a refluxing suspension of the catalyst in a similar solvent.

Also, for example, if desired, compounds of the formula (I) wherein X is CO and Y is $-C\equiv C-$ may be reduced to compounds wherein Y is $-CH=CH-$ in known manner. Suitably this reaction is carried out using catalytic hydrogenation, such as Lindlar catalysis. When Y is $-CH=CH-$, it may be reduced to $-CH_2-CH_2-$ in known manner, suitably using catalytic hydrogenation such as transition metal catalysis.

Compounds of the formula (I) wherein $R_4$ is hydrogen may be converted to the corresponding compounds wherein $R_4$ is alkyl by conventional alkylation procedures.

The skilled man will appreciate that it may be advisable under some reaction conditions to protect the 15-hydroxy group. Suitable examples of such protected hydroxy groups include readily hydrolysable derivatives such as $C_{1-4}$ acyloxy, example acetyloxy, and hydroxy groups etherified by readily removable inert groups such as benzyl or like groups. The protecting groups when present can be removed at the end of the reaction in the usual manner, for example by hydrolysis or hydrogenolysis.

It will be appreciated that compounds of the formula (II) are novel compounds and useful intermediates, and as such form an important part of this invention.

The salts of the compounds of the formula (I) may be prepared in conventional manner, for example by reacting the chosen compound of the formula (I) with a base or an acid as appropriate.

The intermediates of formula (II) may themselves be prepared by the cyclisation of a compound of formula (III):

$$R_{12}O_2C\diagdown\overset{H}{\underset{X'}{\diagup}}\overset{CH_2-Y-(CH_2)_nCN}{\underset{R_{11}}{\diagdown}}\overset{}{\underset{R_3}{\diagup}}R_2 \quad (III)$$

wherein X' is CO or CS and $R_{12}$ is a group such that $CO_2R_{12}$ is an ester group containing no more than twelve carbon atoms; and thereafter if necessary converting a thus formed compound wherein X is CS to the corresponding compound wherein X is $CH_2$.

When $R_4$ is alkyl in the desired compound of formula (II), then the compound of the formula (III) is conveniently prepared in situ during the reaction of a compound of the formula (IV):

$$R_{12}O_2C\diagdown\underset{H}{\overset{N}{\diagup}}\overset{CH_2-Y-(CH_2)_nCN}{\underset{R_{11}}{\diagdown}}\overset{}{\underset{R_3}{\diagup}}R_2 \quad (IV)$$

with $R_{13}NCX^1$ wherein $R_{13}$ is $C_{1-6}$ alkyl and $X^1$ is O or S.

This preferred process is suitably carried out under reflux in an inert solvent such as benzene or toluene or the like. It should be stated that when in this reaction $R_{13}$ is a sterically hindered group then this reaction may proceed only as far as the uncyclised compound of formula (III), in which case the necessary cyclisation of the compound (III) can be achieved with a strong base, such as sodium hydride or sodium ethoxide, in a dry organic solvent. Sodium ethoxide in benzene, or potassium t-butoxide in toluene, benzene or hexamethyl phosphoramide are suitable reagents.

When $R_4$ is hydrogen in the desired compound of formula (III), then the compound of formula (III) is is conveniently formed in situ during the reaction of a compound of formula (IV) with a salt $M^+-CNX^1$ wherein $M^+$ is a metal ion, preferably potassium, in the presence of acid. The acid for this reaction is suitably provided by using an acid addition salt of the compound of formula (IV), or by carrying out the reaction in aqueous acid.

Preferably $R_{12}$ is a $C_{1-6}$ alkyl group such as methyl or ethyl.

The further reductive desulphurisation, if necessary, may be carried out in the manner hereinbefore described.

Intermediates of formula (IV) may be prepared in any convenient manner.

We have found that one suitable method for the preparation of these compounds of the formula (IV) comprises reacting a compound of formula (V): $QCH_2CH_2CR_2R_3R_{11}$ with a compound of formula (VI): $R_{12}O_2C.CH(NH_2)CH_2Y(CH_2)_nCN$, wherein the variable groups are as defined and Q is a good leaving group.

Suitably Q is tosylate or a halide, or like readily displaceable group.

This displacement reaction may be carried out under conventional conditions for such reactions, for example in an organic solvent in the presence of sodium iodide and potassium carbonate.

Compounds of the formula (V) are either known compounds or may be prepared in analogous methods to known compounds.

Compounds of the formula (VI) may be prepared by cleavage of a compound of formula (VII):

$$R_{12}O_2C\diagdown\underset{\overset{N}{\overset{\parallel}{CHPh}}}{\overset{CH_2-Y-(CH_2)_nCN}{\diagup}} \quad (VII)$$

Suitably this cleavage is carried out with mild acid catalysis, for example by chromatography an acid washed silica gel.

Compounds of the formula (VII) may themselves be prepared by reacting a compound of formula (VIII):

$$R_{12}O_2C\diagdown\underset{\overset{\parallel}{CHPh}}{\overset{N}{\diagup}} \quad (VIII)$$

with a compound of formula (IX): $QCH_2Y(CH_2)_nCN$, wherein Q is as hereinbefore defined; in normal manner for such alkylation reactions, for example as hereinbefore described.

Another suitable method for the preparation of these compounds of the formula (IV) comprises reacting a compound of formula (X):

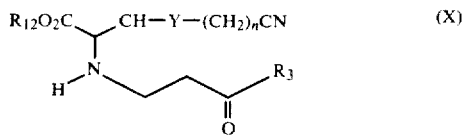

with
(i) a reducing agent to give a compound of formula (IV) wherein $R_2$ is hydrogen; or
(ii) a Grignard reagent of the formula $R_{13}Mg^+X^-$ wherein $R_{13}$ is a $C_{1-6}$ alkyl group and X is a halogen.

The reduction (i) may be carried out by conventional methods for reducing a ketone to an alcohol, for example by sodium borohydride reduction.

The Grignard reaction (ii) may be carried out under conventional conditions for such reactions, for example is an inert anhydrous solvent such as diethyl ether at reflux temperatures.

The compound of formula (X) may be prepared by the reaction of a compound of formula (XI): $CH_2=CH-COR_3$ with a compound of formula (VI) as hereinbefore defined, in an organic solvent such as ethanol at a temperature of $-25°-25°$ C.

It will be realised that when $R_2$ is hydrogen in the resulting compound of formula (I), the compound of formula (X) may be conveniently be prepared in situ and reduced to the compound of formula (IV).

Compounds of the formula (XI) are either known compounds or may be prepared by analogous methods to known compounds. The preparation of compounds of the formula (VI) is described hereinbefore.

In an alternative preparative procedure, which forms an aspect of this invention, the desired compound of the formula (I) is prepared by a process which comprises the cyclisation of a compound of the formula (XII):

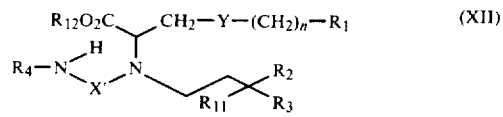

and thereafter if necessary converting a thus formed X is CS compound to the corresponding X is $CH_2$ compound; and if desired converting one group Y or $R_4$ into another group Y or $R_4$, or deprotecting a protected $R_{11}$ hydroxy group.

This cyclisation reaction, and the preparation of the compound of the formula (X) from a compound of formula (XIII):

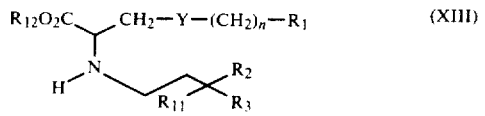

may be carried out in analogous manner to the previously described cyclisation of, and preparation of, compounds of the formula (III).

The preparation of compounds of the formula (XIII) may be carried out in a manner analogous to the preparation of the corresponding compounds of formula (IV) as hereinbefore described.

The necessary formation of the group $R_1$ in the intermediates used in this preparative sequence may be carried out at any convenient stage, by reactions as hereinbefore described in relation to compounds of the formula (II).

It will be appreciated that when $R_1$ contains a free amino group, then it may be necessary or advisable to protect such a group during the preparative sequence in conventional manner.

Such protecting groups include the benzyloxycarbonyl group or a substituted benzyloxycarbonyl group removable by catalytic hydrogenation.

Other suitable protecting groups include those removed by mild acid or alkaline hydrolysis. These include 2-benzene sulphonyl substituted ethoxycarbonyl groups, which may be removed by mild alkaline hydrolysis.

It will be realised that compounds of the formula (I) wherein $R_1$ is $CH_2NHCO_2R^1{}_9$ where $R^1{}_9$ is substituted $C_{1-6}$ alkyl or optionally substituted benzyl as hereinbefore defined are useful intermediates in the preparation of other compounds of the formula (I) wherein $R_1$ is $CH_2NH_2$.

Compounds of the formula (I) have useful pharmacological activity. For example compounds of the formula (I) have anti-gastric acid secretion activity e.g. anti-ulcer activity, cardiovascular activity e.g. antihypertensive activity, platelet aggregation inhibition activity, affect the respiratory tract, e.g. bronchodilator activity, anti-fertility activity, smooth muscle activity and/or anti-arrhythmic activity.

The compounds of the formula (I) are especially useful as bronchodilation agents.

In general it may be said that compounds of the formula (I) have a range of pharmacological activities similar to those shown by the natural prostaglandins, but that their activity profiles tend to be rather more selective so that each compound tends to have a major activity readily ascertained by routine pharmacological tests.

The invention therefore also provides a pharmaceutical composition comprising a compound of the formula (I) and a pharmaceutically acceptable carrier.

The compounds of the formula (I) also have good stability.

In order to utilise the selectivity of activity found with compounds of the formula (I), normally a given compound will be used in the treatment of the disorder corresponding to the compound's major activity (that is, the disorder for which the compound has the lowest active dose) and will accordingly be formulated into the corresponding pharmaceutical composition, and administered in a manner conventional for treatment of that disorder. It may also of course be possible with compounds having one or more further pronounced activities to formulate and use the compound for those further activities as well as for the major activity, provided that there is no undesirable pharmacological interaction between the different activities, or that separation of the different activities can be obtained by a difference in the formulation or in the mode of administration.

The composition may be in the form of tablets, capsules, powders, granules, lozenges or liquid preparations, such as oral or sterile parenteral solutions or suspensions.

Tablets and capsules for oral administration may be in unit dose presentation form, and may contain conventional excipients such as binding agents, fillers, tabletting lubricants, disintegrants, and acceptable wetting agents and the like. The tablets may be coated according to methods well known in normal pharmaceutical practice. Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, emulsifying agents, non-aqueous vehicles (which may include edible oils), preservatives, and if desired conventional flavouring or colouring agents, and the like.

For parenteral administration, fluid unit dosage forms are prepared utilising the compound of the formula (I) and a sterile vehicle. The compound, depending on the vehicle and concentration used, can be either suspended or dissolved in the vehicle. In preparing solutions the compound can be dissolved for injection and filter sterilised before filling into a suitable vial or ampoule and sealing. Advantageously, adjuvants such as a local anaesthetic, preservatives and buffering agents can be dissolved in the vehicle. Parenteral suspensions are prepared in substantially the same manner except that the compound is suspended in the vehicle instead of being dissolved and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

When appropriate, the compositions of this invention may be presented as an aerosol for oral administration, or as a microfine powder for insufflation.

As is common practice, the compositions will usually be accompanied by written or printed directions for use in the medical treatment concerned.

It will of course be realised that the precise dosage used in the treatment of any of the hereinbefore described disorders will depend on the actual compound of the formula (I) used, and also on other factors such as the seriousness of the disorder being treated.

The invention also provides a method of treatment and/or prophylaxis of disorders in human beings or animals which comprises the administration to the sufferer of an effective amount of a compound of the formula (I). Normally the compounds will be used in the therapy of human disorders.

Intermediates of the formula (II) also have pharmaceutical behaviour similar to that of compounds of the formula (I), and as such form an aspect of the present invention.

The following Examples illustrate the preparation of compounds of the formula (I) and their pharmacological properties.

EXAMPLE 1 (a)

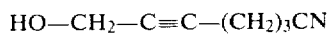

To a stirred slurry of sodium cyanide (15 g, 306 mmol) in dimethyl sulphoxide (100 ml) preheated to 85° C., was added 1-tetrahydropyranyloxy-6-chloro-hex-2-yne (66.2 g, 306 mmol) at such a rate as to keep the temperature between 85° C. and 100° C. One hour after the addition was completed, the cooled mixture was slowly added to brine (600 ml) and extracted with ether (3×200 ml). The combined ether extracts were washed with further brine (200 ml) and dried over sodium sulphate. After removal of the solvent under reduced pressure, the reddish-brown oil was distilled and the fraction boiling between 140° and 160° C. (0.25 m.m.) collected and dissolved in methanol (200 ml). This solution was stirred overnight with 5 M$H_2SO_4$ (30 ml) and neutralised with solid potassium carbonate. The methanol was removed under reduced pressure and the residue partitioned between ether (200 ml) and brine (300 ml). The aqueous layer was extracted with further ether (2×300 ml). The combined organic extracts were washed with brine (2×100 ml) and dried over sodium sulphate. Removal of the solvent under reduced pressure, and distillation of the oil obtained gave 6-cyano-hex-2-yn-1-ol (22.0 g, 58%) as a colourless oil.

I.R. (cm$^{-1}$) 3400 (—OH), 2250 (CN).

N.M.R. ($\tau$) 5.2 (brs, HO—$\underline{CH_2}$—C≡C—), 7.1 (brs, $\underline{H}$—O.

EXAMPLE 1 (b)

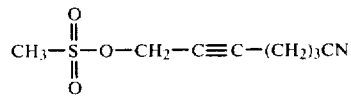

To a stirred solution of 6-cyano-hex-2-yn-1-ol (18.0 g 146 mmol) in dry methylene chloride (100 ml) containing dry triethylamine (30 ml) was added methanesulphonyl chloride (17.0 g 149 mmol) in dry methylene chloride (50 ml) over fifteen minutes at 0° C. (ice-salt bath), under nitrogen. After a further five minutes, a precipitate appeared and the solution became yellow-/orange in colour. The solution was stirred for twenty five minutes after the addition was completed, poured into ether (600 ml) and washed with ice-cold water (50 ml). The slightly cloudy organic layer was then washed with 0.05 N hydrochloric acid (50 ml), brine (2×50 ml), sodium bicarbonate (40 ml) and brine (40 ml) and dried over sodium sulphate. Removal of the solvent under reduced pressure gave a light yellow oil that was used without further purification.

N.M.R. ($\tau$) 5.16 (brm, —O—$\underline{CH_2}$—C≡C—), 6.91(s, $\underline{CH_3}$—$SO_2$—O—).

EXAMPLE 1 (c)

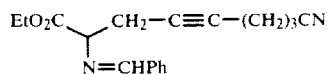

The N-benzylidene derivative of glycine ethyl ester, (prepared as described by G. Stork, et al, *J. Org. Chem.* 41, 3491 (1976)) (30.2 g 158 mmol) in dry tetrahydrofuran (60 ml) was added dropwise to a stirred suspension of potassium t-butoxide (18.1 g, 160 mmol) in dry tetrahydrofuran (60 ml) under nitrogen at −78° C. The solution immediately became bright red in colour. After thirty minutes, sodium iodide (3 g) was added to the solution, followed by the dropwise addition of 1-methanesulphonyloxy-6-cyano-hex-2-yne (the entire product from the previous reaction) in dry tetrahydrofuran (100 ml). The solution was stirred at −78° C. for one hour and allowed to warm up to room temperature over two hours. The solution was stirred for a further three hours then saturated brine (100 ml) and ether (300 ml) were added. The organic layer was washed with brine until neutral and dried over sodium sulphate. Removal of the solvent under reduced pressure (below 30° C.) gave ethyl 2-(benzylidene-amino)-8-cyano-oct-4-ynoate as a red oil.

N.M.R. (τ) 1.71 (S, 1H, PhC$\underline{H}$=N—), 5.80 (q, 2H, CO$_2$—C$\underline{H}_2$—CH$_3$).

EXAMPLE 1(d)

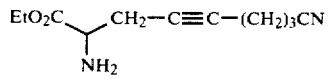

Ethyl 2-(benzylideneamino)-8-cyano-oct-4-ynoate (the entire product from the above reaction) was coated onto acid-washed silica gel (Merck: Kieselgel60) (135 g) using chloroform as solvent. This material was packed above a further (135 g) of silica gel. After elution of benzaldehyde with 90% pentane/10% ether, elution with 90% ether/10% methanol gave ethyl 2-amino-8-cyano-oct-4-ynoate (21.0 g, 69% overall from 6-cyano-hex-4-yn-1-ol) as a light red oil.

N.M.R. (τ) 5.75 (q., 2H, —CO$_2$—C$\underline{H}_2$—CH$_3$), 6.41 (t. 1H, NC$\underline{H}$) 8.21 (S, 2H, —NH$_2$ removed by D$_2$O).

EXAMPLE 1(e)

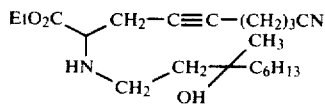

A solution of ethyl 2-amino-8-cyano-oct-4-ynoate (14.2 g, 68 mmol) and 1-(p-toluenesulphonyl)-3-methyloctan-3-ol (23.5 g. 72 mmol) in dry acetonitrile (250 ml) was stirred at room temperature, under nitrogen, with sodium iodide (12.1 g 81 mmol) and potassium carbonate (10.0 g, 71 mmol). After four hours the mixture was heated and stirred overnight on an oil bath (bath temperature 110° C.). The mixture was cooled and poured into saturated brine (200 ml). Extraction with ether (3×200 ml), followed by washing the combined organic layers with further brine (3×80 ml) gave a dark red solution that was dried over sodium sulphate. Evaporation of the solvent under reduced pressure, and chromatography on silica gel (240 g) using 70% hexane/3-0%ethyl acetate as eluant gave ethyl 8-cyano-2-[(3'-hydroxy-3'-methyl-n-nonyl)amino]-oct-4-ynoate (13.9 g, 56%) as a dark orange oil.

I.R. (cm$^{-1}$) 3300 (OH), 2240 (CN), 1735 (C=O).

H.R.M.S. m/e C$_{21}$H$_{37}$N$_2$O$_3$ (M+H)$^+$ requires 365.2802, found 365.2795.

EXAMPLE 1(f)

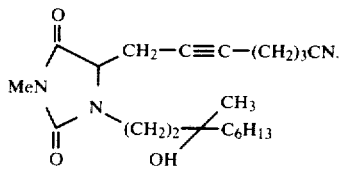

Ethyl 8-cyano-2-[3'-hydroxy-3'-methyl-n-nonyl)amino]-oct-4-ynoate (17.0 g, 47 mmol) was refluxed with methyl isocyanate (3.5 g, 61 mmol) for four hours in dry toluene (150 ml). The toluene was removed under reduced pressure, and the oil obtained was chromatographed on silica gel (145 g) using 50% hexane/50% ethyl acetate as eluent to give 1-(3'-hydroxy-3'-methyl-n-nonyl)-3-methyl-5-(6"-cyano-n-hex-2"-ynyl)-hydantoin (12.5 g, 64%) as an orange oil.

I.R. (cm$^{-1}$) 3450 (OH), 1765,

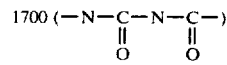

N.M.R. (τ)

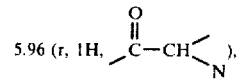

7.00 (s, 3H, CH$_3$N).

H.R.M.S. m/e C$_{21}$H$_{33}$N$_3$O$_3$ requires 375.2522, found 375.2517.

EXAMPLE 1(g)

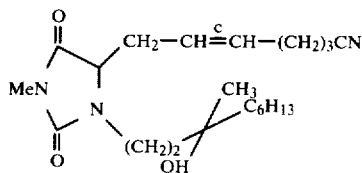

1-(3'-hydroxy-3'-methyl-n-nonyl)-3-methyl-5-(6"-cyano-n-hex-2"-ynyl)-hydantoin (0.8 g. 2 mmol) was shaken in ethanol (40 ml) containing palladium on calcium carbonate (50 mg) and quinoline (1 ml) under a hydrogen atmosphere. Uptake of hydrogen was completed in two hours. The mixture was filtered through kieselguhr and the ethanol was removed under reduced pressure. The residue was taken up into ether (250 ml) and the solution was washed with 1 M hydrochloric acid (20 ml), brine (20 ml), saturated sodium bicarbonate (100 ml) and brine (50 ml). The ether solution was dried over sodium sulphate, the solvent removed under reduced pressure and the product chromatographed on silica gel (25 g), using ethyl acetate as eluant to give 1-(3'-hydroxy-3-methyl-n-nonyl)-3-methyl-5-(6"-cyano-n-hex-2"-enyl)hydantoin (690 mg) as a yellow oil.

I.R. (cm$^{-1}$) 3430 (OH), 1765,

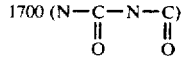

N.M.R. (τ) 4.58 (2H, m, vinyl protons),

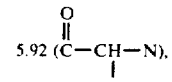

7.02 (CH$_3$N).

H.R.M.S. C$_{21}$H$_{36}$N$_3$O$_3$ requires 378.2755, found 378,2769 (M+H)$^+$.

EXAMPLE 1(h)

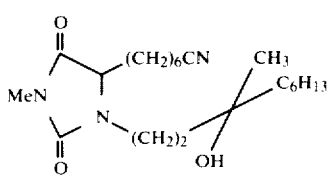

1-(3'-hydroxy-3'-methyl-n-nonyl)-3-methyl-5-(6"-cyano-n-hex-2"-ynyl) hydantoin (1.0 g, 2.4 mmol) in anhydrous ethanol (30 ml) containing palladium (10%) on charcoal (50 mg) was shaken under a hydrogen atmosphere for two hours, at which time the uptake of hydrogen had stopped. The mixture was filtered through kieselguhr and the solvent was evaporated under reduced pressure. Chromatography on silica gel (30 g) using ethyl acetate as eluant gave 1-(3'-hydroxy-3'-methyl-n-nonyl)-3-methyl-5-(6"-cyano-n-hexyl)-hydantoin (0.98 g, 97%) as a pale yellow oil.

I.R. (cm$^{-1}$) 3400 (OH), 1765,

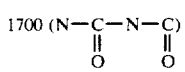

N.M.R. ($\tau$)

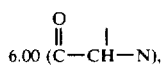

7.02 (CH$_3$N).

H.R.M.S. C$_{21}$H$_{38}$N$_3$O$_3$ requires 380.2913, found 380.2903 (M+H)$^+$.

EXAMPLE 1(i)

Compound 1

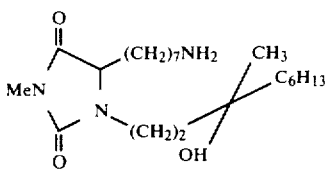

1-(3'-hydroxy-3'-methyl-n-nonyl)-3-methyl-5-(6"-cyano-n-hex-2"-ynyl)-hydantoin (2.0 g, 5.3 mmol) in ethanol (50 ml) containing two equivalents of dry hydrogen chloride and platinum dioxide (50 mg), was shaken under a hydrogen atmosphere for five hours. The solution was decanted from the catalyst, and the ethanol was removed under reduced pressure. The residue was dissolved in 1 M aqueous hydrochloric acid (50 ml). This solution was washed with ether (2×50 ml) and then made basic with potassium carbonate. The basic solution was extracted with ether (3×100 ml) and the combined ether extracts were washed with brine (50 ml) and dried over sodium sulphate. Removal of the solvent under reduced pressure gave 1-(3'-hydroxy-3'-methyl-n-nonyl)-3-methyl-5-(7"-amino-n-heptyl)-hydantoin (1.0 g, 49%) as a very pale yellow oil.

I.R. (cm$^{-1}$) 3450-3200 (NH,OH), 1765,

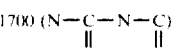

N.M.R. ($\tau$)

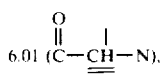

7.01 (CH$_3$N).

H.R.M.S. C$_{21}$H$_{41}$N$_3$O$_3$ requires 383.3146, found 383.3153.

EXAMPLE 2

Compound 2

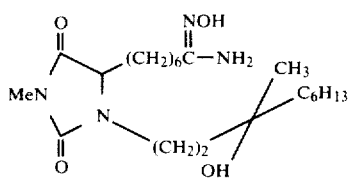

A solution of 1-(3'-hydroxy-3'-methyl-n-nonyl)-3-methyl-5-(6"-cyano-n-hexyl)-hydantoin (2.1 g, 5.5 mmol) and hydroxylamino hydrochloride (0.39 g, 5.6 mmol) were heated in dry ethanol at 50° C. Sodium hydroxide (0.22 g, 5.5 ml) in dry ethanol (10 ml) was then added. After a further one hour the mixture was refluxed for sixteen hours, cooled, further hydroylaminehydrochloride (0.89 g, 12.8 mmol) and sodium hydroxide (0.55 g, 13.8 mmol) added and the solution refluxed for a further four hours. The ethanol was removed under reduced pressure and the residue taken up in ether (250 ml). This solution was washed with brine (2×50 ml) and dried over sodium sulphate. Removal of the solvent under reduced pressure and chromatography of the yellow gum obtained on silica gel (30 g) using ethylacetate, 2% ethanol as eluent gave 1-(3'-hydroxy-3'-methyl-n-nonyl)-3-methyl-5-(6"-amidoxyl-n-hexyl)-hydantoin (1.0 g) as a colourless oil.

I.R. ($\nu_{max}$) cm$^{-1}$ 3450, 3375, 3200 (amidoxyl O-H and N-H), 1765 and

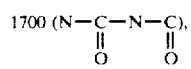

1660 (C=N).

N.M.R. $\tau$5.40 (2H, bm, NH$_2$),

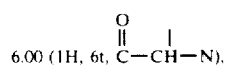

7.98 (3H, s, CH$_3$—N).

H.R.M.S. 412.3039 C$_{21}$H$_{40}$N$_4$O$_4$ requires 412.3047.

EXAMPLE 3

Compound 3

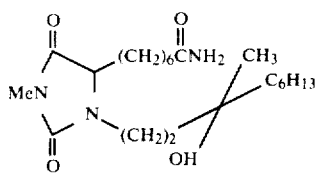

A solution of 1-(3'-hydroxy-3'-methyl-n-nonyl)-3-methyl-5-(6''-cyano-n-hexyl) hydantoin (1.0 g, 2.6 m mol) in analar acetone (25 ml) was added to aqueous hydrogen peroxide (15%, 6 ml). The solution was stirred at room temperature and 10% aqueous potassium carbonate solution (3 ml) added. After 24 hours, the acetone was removed under reduced pressure (at 25° C.) and the residue taken up in ether (250 ml). This solution was washed with brine (3×40 ml) and dried over sodium sulphate. (The solution was tested with aqueous acidic starch-iodide paper) The solvent was removed under reduced pressure and the oil chromatographed on silica gel (20 g) using ethyl acetate, then ethyl acetate 2% ethanol as eluent to give 1-(3'-hydroxy-3'-methyl-n-nonyl)-3-methyl-5-(6''-amidoyl-n-hexyl) hydantoin (0.72 g, 69%) as a pale yellow oil.

I.R. ($\nu_{max}$) cm$^{-1}$ 1765 and

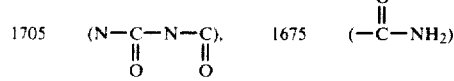

N.M.R. ($\tau$) 4.25 (2H, b, NH$_2$),

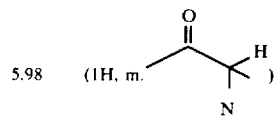

7.00 (3H, s, CH$_3$-N).

H.R.M.S. Found 397.2960, C$_{21}$H$_{39}$N$_3$O$_4$ requires 397.2940.

ANALYSIS C$_{21}$H$_{39}$N$_3$O$_4$ requires C,63.45, N,10.57, H,9.89. Found C,63.00, N,10.52, H,9.87.

EXAMPLE 4

Compound 4

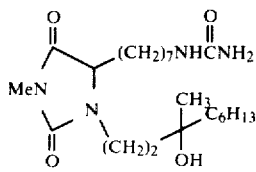

1-(3'-Hydroxy-3'-methyl-n-nonyl)-3-methyl-5-(7''-amino-n-heptyl) hydantoin (1.0 g, 2.6 mmol) in methanol (10 ml) was stirred at 0° C. and aqueous hydrochloric acid (2 M, 2.6 ml, 5.2 mmol) was added dropwise over five minutes. After a further thirty minutes an aqueous solution of potassium cyanate (0.5 M, 10.4 ml, 5.2 mmol) was added dropwise over half an hour. The mixture was stirred overnight, the methanol was removed under reduced pressure and the aqueous layer was extracted with ether (3×50 ml). The combined ether Layers were washed with brine (2×50 ml) and dried over sodium sulphate. Removal of the solvent under reduced pressure gave an oil that was chromatographed upon silica gel (18 g) using ethyl acetate and ethyl acetate: 3% ethanol as eluants. 1-(3'-Hydroxy-3'-methyl-n-nonyl)-3-methyl-5-(7''-ureido-n-heptyl) hydantoin (0.7 g, 63%) was obtained as a very pale yellow oil.

I.R. (cm$^{-1}$) 3450 (OH); 3350 (NH); 1765 and 1700 (hydantoin C=O stretch);

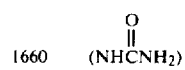

N.M.R. ($\tau$)

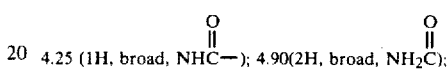

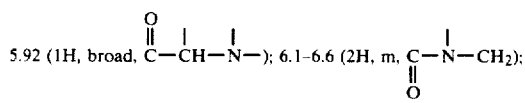

6.78(2H, m, CH$_2$NH); 7.00(3H, s, CH$_3$—N);

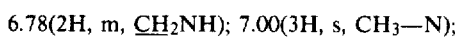

9.1(3H, t, terminal methyl).

H.R.M.S.: C$_{22}$H$_{42}$N$_4$O$_4$ requires 426.3203. Found 426.3201.

EXAMPLE 5

Compound 5 and Compound 6

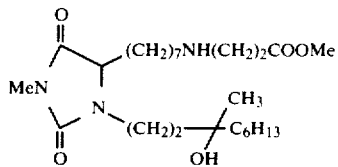

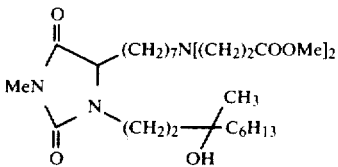

Methyl acrylate (0.3 g, 3.5 mmol) was added, in one portion, to a stirred solution of 1-(3'-hydroxy-3'-methyl-n-nonyl)-3-methyl-5-(7''-amino-n-heptyl) hydantoin (0.9 g, 2.3 mmol) in dry methanol (20 ml) at room temperature. The mixture was stirred for two and a half hours at room temperature and the methanol was removed under reduced pressure. The residual dark brown oil was chromatographed on silica gel (19 g) using ethyl acetate and ethyl acetate: 3% ethanol as eluants. This gave 1-(3'-hydroxy-3'-methyl-n-nonyl)-3-methyl-5-(7''-(2'''-methoxycarbonylethyl)amino-n-heptyl) hydantoin (680 mg) (compound 5) as a brown oil):

I.R. (cm$^{-1}$): 3400(OH, NH); 1765 and 1705 (hydantoin C=O stretch) 1735 (COOMe).

N.M.R. (τ): 5.99(1H, m, COC$\underline{H}$-N); 6.32(3H, s, COOMe);

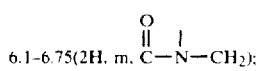
6.1-6.75(2H, m, C-N-CH$_2$);

7.00(3H,s,CH$_3$N); 7.1-7.6 (6H, 2×C$\underline{H}_2$N and C$\underline{H}_2$CO$_2$Me);

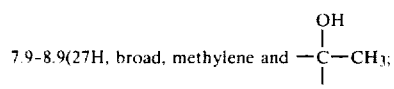
7.9-8.9(27H, broad, methylene and -C-CH$_3$;

9.1(3H, t, terminal methyl).

H.R.M.S.: C$_{25}$H$_{47}$N$_3$O$_5$ requires 469.3513; found 469.3489

Analysis: C$_{25}$H$_{47}$N$_3$O$_5$ requires: C, 63.93; N, 8.95; H, 10.09%. Found: C, 63.17; N, 8.33; H, 9.94%.

Also eluted was 1-(3'-hydroxy-3'-methyl-n-nonyl)-3-methyl-5-(7''-(bis(2'''-methoxycarbonylethyl)amino-n-heptyl) hydantoin (400 mg) (compound 6) as a pale yellow oil.

I.R. (cm$^{-1}$): 3420 (OH); 1760 and 1700 (hydantoin C=O stretch) and 1735 (COOMe).

N.M.R. (τ): 5.93(1H, m, COC$\underline{H}$-N); 6.32(6H, s, 2×COOMe);

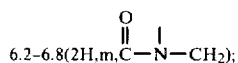
6.2-6.8(2H,m,C-N-CH$_2$);

7.00(3H, s, CH$_3$N); 7.1-7.6 (10H, 3×CH$_2$N and 2×CH$_2$COOMe);

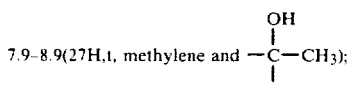
7.9-8.9(27H,t, methylene and -C-CH$_3$);

9.1(3H, t, terminal methyl).

H.R.M.S.: C$_{29}$H$_{53}$N$_3$O$_7$ requires: 555.3880; found 555.3885.

Analysis: C29H53N3O7 requires: C, 62.90; N, 7.59; H, 9.28%. Found: C, 62.94; N, 7.17; H, 9.66%.

EXAMPLE 6

Compound 7

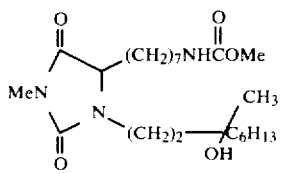

Methyl chloroformate (0.49 g, 5.2 mmol) and anhydrous sodium carbonate (2.0 g) were added in one portion to a stirred solution of 1-(3'-hydroxy-3'-methyl-n-nonyl)-3-methyl-5-(7''-amino-n-heptyl)hydantoin (2.0 g, 5.2 mmol) in dry methanol (20 ml). After five minutes, the mixture was heated to reflux. One and a half hours later, the mixture was cooled, poured into iced water (100 ml) and extracted with ether (3×100 ml). The combined ether extracts were washed with brine (2×75 ml) and dried over sodium sulphate. The solvent was removed under reduced pressure and the pale brown oil obtained was chromatographed on silica gel (60 g) using ethanol acetate hexane (1:1) as eluant to give 1-(3'-hydroxy-3'-methyl-n-nonyl)-3-methyl-5-(7'-methoxycarbonylamino-n-heptyl)hydantoin (1.0 g) as a very pale yellow oil.

I.R. (cm$^{-1}$): 34.50 (OH); 3350 (NH); 1760 (hydantoin C=O stretch); 1700 (hydantoin and carbonate C=O stretch).

N.M.R. (τ): 5.14-5.45 (1H, broad, NH removed by D$_2$O after shaking)

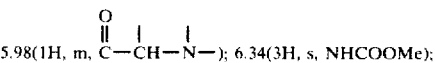
5.98(1H, m, C-CH-N-); 6.34(3H, s, NHCOOMe);

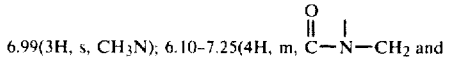
6.99(3H, s, CH$_3$N); 6.10-7.25(4H, m, C-N-CH$_2$ and

CH$_2$NHC-);

8.0-9.2 (31H, broad, residual protons).

H.R.M.S.: C$_{23}$H$_{43}$N$_3$O$_5$ requires: 441.3202; found 441.3192

Analysis: C$_{23}$H$_{43}$N$_3$O$_5$ requires: C, 62.56; N, 9.52; H, 9.81%. Found: C, 62.31; N, 8.93; H, 9.98%.

EXAMPLE 7

Compound 8

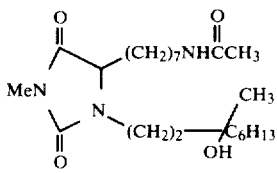

Acetic anhydride (0.54 g, 5.3 mmol) was added in one portion to a cooled (5° C.) solution of 1-(3'-hydroxy-3'-methyl-n-nonyl)-3-methyl-5-(7''-amino-n-heptyl)hydantoin (2.0 g, 5.2 mmol) in dry pyridine (8 ml). The reaction initially became warm (50° C.) and then was cooled. After stirring at room temperature for eighteen hours, the mixture was diluted with ether (200 ml) and was washed successively with aqueous hydrochloric acid (5M, 40 ml), water (2×20 ml), 5% sodium bicarbonate solution (40 ml), and brine (50 ml). The solution was dried over sodium sulphate, the solvent was removed under reduced pressure and the dark oil so obtained was chromatographed on silica gel (40 g) using ethyl acetate and ethyl acetate:5% ethanol as eluants. The dark oil (1.2 g) obtained was distilled on a molecular still (distillation temperature 180°-200° C., 2 μBars) to give 1-(3'-hydroxy-3'-methyl-n-nonyl)-3-methyl-5-(7''-acetamido-n-heptyl)hydantoin (0.55 g) as a pale yellow oil.

I.R. (cm$^{-1}$): 3450 (OH); 3325 (NH); 1765 and 1700 (hydantoin C=O stretch); 1660 (amide C=O).

N.M.R. (τ):

4.20-4.65(1H, broad, NH);

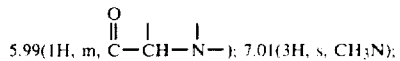
5.99(1H, m, C-CH-N-); 7.01(3H, s, CH$_3$N);

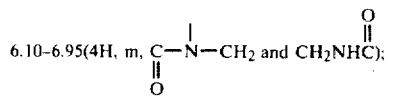

8.03 (1H, broad, OH, removed by D₂O);

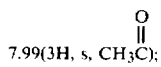

9.1 (3H, t, terminal methyl), 8.0-8.9 (28H, m, residual protons).

H.R.M.S.: $C_{23}H_{43}N_3O_4$ requires: 425.3251. Found: 425.3276.

EXAMPLE 8

Compound 9 and Compound 10

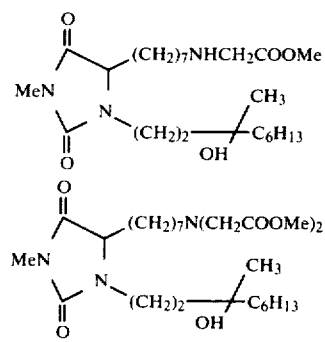

Methyl bromoacetate (0.45 ml, 5.3 mmol) and anhydrous sodium carbonate (1.5 g) were added in portions to a stirred solution of 1-(3'-hydroxy-3'-methyl-n-nonyl)-3-methyl-5-(7''-amino-n-heptyl)hydantoin (2.0 g, 5.2 mmol) in dry methanol (15 ml). After five minutes, the mixture was heated to reflux. After one and a half hours, the mixture was diluted with ether (250 ml) and washed with brine (3×60 ml). The solution was dried over sodium sulphate and evaporated under reduced pressure to give a dark oil (1.8 g) which was chromatographed on silica gel (85 g) using ethyl acetate; pentane (1:1), ethyl acetate, ethyl acetate:2% ethanol, ethyl acetate:5% ethanol and ethyl acetate:12% ethanol as successive eluants. This gave 1-(3'-hydroxy-3'-methyl-n-nonyl)-3-methyl-5-5-[7'-(N-methoxycarbonylmethyl-)amino-n-heptyl]-hydantoin. (1.0 g) (compound 9) as a dark brown oil. The dark oil was passed through neutral alumina (50 g) using chloroform as eluant to give a pale red oil (1.0 g). The spectroscopic properties of this red oil were identical with those of the dark brown oil.

I.R. (cm⁻¹): 3450 (OH); 3350 (NH); 1765 and 1700 (hydantoin C=O stretch); 1740 (COOMe).

N.M.R. (τ):

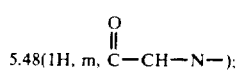

6.28 (3H, s, COOMe); 6.62 (2H, s, NHC$\underline{H}$₂COOMe); 7.00 (3H, s, CH₃N);

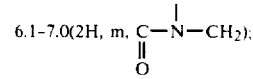

7.41 (2H, m, C$\underline{H}$₂NHCH₂COOMe reduced to a triplet after D₂O shake); 8.14 (2H, t, OH, NH, removeably D₂O); 8.10-9.25 (31H, broad, residual protans).

H.R.M.S.: $C_{24}H_{45}N_3O_5$ requires: 455.3357. Found: 455.3356.

Analysis: $C_{24}H_{45}N_3O_5$ requires: C, 63.27; N, 9.22; H, 9.95%. Found: C, 63.60; N, 9.64; H. 10.33%.

Also eluted was 1-(3'-hydroxy-3'-methyl-n-nonyl)-3-methyl-5-{7'-[N,N-bis(methoxycarbonylmethyl-)amino]-n-heptyl}hydantoin (0.5 g) (Compound 10) as a pale yellow oil.

I.R. (cm⁻¹) 3450 (O-H); 1765 and 1700 (hydantoin C=O stretch); 1740 (COOMe).

N.M.R. (τ):

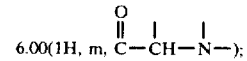

6.29 (6H, s, 2×COOMe); 6.46 (4H, s, 2×NC$\underline{H}$₂COOMe); 7.00 (3H, s, CH₃N); 7.32 (2H, m, C$\underline{H}$₂NH CH₂COOMe); 8.20 (1H, t, OH, removed by D₂O); 8.1-9.2 (31H, t, residual protons)

H.R.M.S.: $C_{27}H_{49}N_2O_3$ requires: 527.3570. Found: 527.3614.

Analysis: $C_{27}H_{49}N_2O_7$ requires C, 61.45; N, 7.96; H, 9.36%. Found: C, 61.75; N, 7.46; H, 10.10%.

EXAMPLE 9

Compound 11

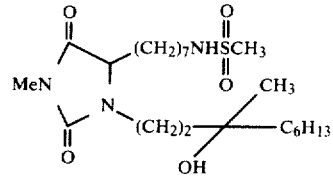

To a solution of 1-(3'-hydroxy-3'-methyl-n-nonyl)-3-methyl-5-(7''-amino-n-heptyl)hydantoin (1.3 g, 3.4 mmol) in dry pyridine, at 5° C., was added methanesulphonyl chloride (0.39 g, 304 mmol) in one portion with stirring. The mixture was stirred for eighteen hours, diluted with ether (250 ml) and washed successively with aqueous hydrochloric acid (5M, 50 ml), brine (2×50 ml), 5% sodium bicarbonate solution (50 ml), and brine (50 ml) and was then dried over sodium sulphate. Removal of the solvent under reduced pressure gave an oil that was chromatographed on silica gel (45 g) using ethyl acetate:pentane (1:1), ethyl acetate and ethyl acetate: 1% ethanol as eluants. Such a procedure gave 1-(3'-hydroxy-3'-methyl-n-nonyl)-3-methyl-5-(7''-methanesulphonylamino-n-heptyl)hydantoin (0.62 g, 40%) as pale yellow oil.

I.R. (cm⁻¹): 3500 (OH); 3300 (NH); 1765 and 1705 (hydantoin C=O stretch).

N.M.R. (τ): 5.2-5.6 (1H, t, NH removed by D₂O);

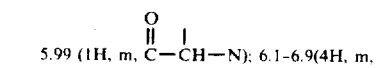

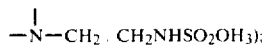

7.00 (3H, s, CH$_3$N); 7.08 (3H, s, CH$_3$SO$_2$); 8.18 (1H, s, OH, removed by D$_2$O); 8.1–9.2 (31H, t, residual protons).

H.R.M.S.: C$_{22}$H$_{41}$N$_3$O$_4$(M$^+$-H$_2$O) requires: 443.2815. Found 443.2817.

EXAMPLE 10

Compound 12

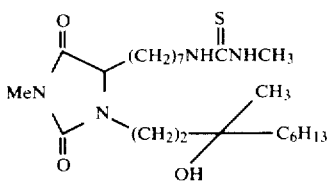

To a stirred solution of 1-(3'-hydroxy-3'-methyl-n-nonyl)-3-methyl-5-(7''-amino-n-heptyl)hydantoin (0.8 g, 2.1 mmol) in dry benzene, at room temperature, was added methyl isothiocyanate (150 mg, 2.6 mmol) in dry benzene (10 ml) in one portion. The solution was stirred for three hours, the benzene was removed and the oil obtained was chromatographed on silica gel (30 g) using ethylacetate:hexane (30:70), (50:50) and (100:0) as successive eluants to give 1-(3'-hydroxy-3'-methyl-n-nonyl)-3-methyl-5-(7''-(N'-methylthiouriedo)-n-heptyl)-hydantoin (0.3 g).

I.R. (cm$^{-1}$): 3450 (OH); 3400 3200 (NH); 1765 and 1700 (hydantoin C=O stretch); 1560 (C=S).

N.M.R. ($\tau$): 3.6–4.3 (2H, NH removed by D$_2$O);

6.00(1H, m, $\overset{O}{\overset{\|}{C}}-\overset{|}{CH}-N$);

6.10–6.90(4H, m, $-\overset{|}{N}-CH_2$ and CH$_2$NH);

7.00 (6H, m, reduced to 2×5 with D$_2$O, CH$_3$N and CH$_3$NH); 7.9–9.2 (31H, t, residual protons).

H.R.M.S.: C$_{23}$H$_{44}$N$_4$O$_3$S requires: 456.3133. Found: 456.3110.

EXAMPLE 11

Compound 13

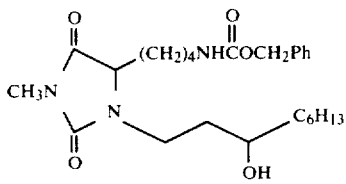

The methyl ester of N-E-carbobenzyloxy-lysine (6.0 g, 20 mmol) in dry ethanol (10 ml), was stirred at 0° C. (ice-bath) and hexylvinyl ketone (2.8 g, 20 mmol) was added dropwise over five minutes. The mixture was stirred for two hours, further dry ethanol (30 ml) was added and the solution cooled to 0° C. Sodium borohydride (0.7 g, 18 mmol) was added in one portion and the mixture stirred for three hours. The solution (at 10° C.) was cooled to 0° C., and acetic acid (5 ml) added dropwise. The mixture was poured into water (100 ml) and brine (100 ml) and extracted with ether (3×120 ml). The combined ether layers were washed with brine and dried over sodium sulphate. Removal of the solvent under reduced pressure gave crude methyl-2-[3'-hydroxy-n-nonyl)amino]-6-carbobenzyloxyamino-hexanoate as a yellow oil (8.5 g). 4.0 g of this oil was treated with methyl iso-cyanate (1 equivalent) in dry benzene (80 ml) at reflux for four hours. The solvent was removed under reduced pressure and the yellow oil that remained was chromatographed on silica gel (90 g) using chloroform 1% methanol as eluant. This gave 1-(3'-hydroxy-n-nonyl)-3-methyl-5-[4''-(N-carbobenzyloxy)-amino-n-butyl]hydantoin. (2.6 g, 59%) as a pale yellow oil.

I.R. (cm$^{-1}$) 3450 (OH); 3325 (NH); 1765, 1700 (hydantoin C=O); 1700 (carbonate C=O).

N.M.R. ($\tau$) 2.66 (5H, s, aromatic protons); 4.97 4.97 (2H, s, OCH$_2$Ph); 6.80 (1H, b, OH (removed by D$_2$O);

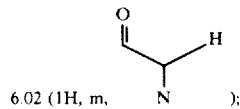

6.02 (1H, m, );

7.02 (3H, s, CH$_3$N).

H.R.M.S. C$_{25}$H$_{39}$N$_3$O$_5$ requires 461.2887. Found 461.2842.

EXAMPLE 12

Compound 14

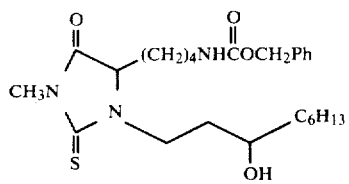

The remaining 4.5 g of crude methyl-2-[(3'-hydroxy-n-nonyl)amino]-6-carbobenzyloxyamino-hexanoate was treated with methyl isothiocyanate (1 equivalent) in dry benzene (80 ml) at reflux for four hours. The solvent was removed under reduced pressure and the yellow-red oil that remained was chromatographed on silica gel (110 g) using chloroform:1% methanol as eluant. This gave 1-(3'-hydroxy-n-nonyl)-3-methyl-5-[4''-(N-carbobenzyloxy)amino-n-butyl]-2-thiohydantoin. (3.75 g, 73%) as a very pale yellow oil.

I.R. (cm$^{-1}$) 3450 (OH); 3350 (NH); 1740 (thiohydantoin C=O); 1700 (carbonate C=O).

N.M.R. ($\tau$) 2.70 (5H, s, aromatic protons); 4.97 (2H, s, OCH$_2$Ph);

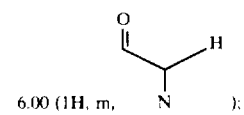

6.00 (1H, m, );

6.80 (3H, s, CH$_3$N).

H.R.M.S. C$_{25}$H$_{39}$N$_3$O$_4$S requires 477.2658. Found 477.2677.

EXAMPLE 13

Compound 15

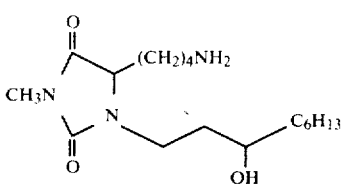

1-(3'-Hydroxy-n-nonyl)-3-methyl-5-(N-carbobenzyloxy)-4''-amino-n-butyl)hydantoin (1.41 g, 3.0 mmol) in dry distilled dimethoxyethene (50 ml) containing 10% Pd/C (100 mg) was shaken under an atmosphere of hydrogen at room temperature for five hours at room temperature. The catalyst was filtered off and the solvent removed under reduced pressure to give 1-(3'-hydroxy-n-nonyl)-3-methyl-5-(4''-amino-n-butyl)-hydantoin (0.95 g, 95%) as a very pale yellow oil.

I.R. (cm$^{-1}$) 3550–2450 (OH, NH very broad due to hydrogen bonding); 1765, 1705 (hydantoin C=O).

N.M.R. ($\tau$) 7.06 (3H, s, CH$_3$N);

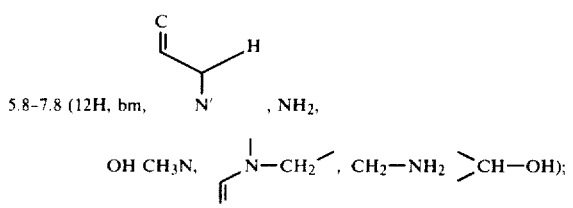

7.9–9.3 (21H, bm, remaining protons).

H.R.M.S. C$_{17}$H$_{33}$N$_3$O$_3$ requires 327.2520. Found 327.2517.

EXAMPLE 14

Compound 16

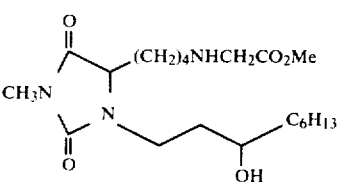

1-(3'-Hydroxy-n-nonyl)-3-methyl-5-[(4''-amino-n-butyl)hydantoin (0.80 g, 2.4 mmol) in dry methanol (20 ml) was stirred with dry sodium carbonate (0.5 g) and methyl bromoacetate (0.37 g, 2.4 mmol) under nitrogen at room temperature. After ten minutes the mixture was refluxed for one and a half hours and cooled then added to water (30 ml) and brine (30 ml). The product was extracted with ether (3 × 80 ml) and the combined ether layers were washed with brine and dried over sodium sulphate. After removal of the solvent under reduced pressure, the oil so obtained (1.2 g) was chromatographed on silica gel (30 g) using ethyl acetate and ethyl acetate/3% methanol as successive eluants. This gave 1-(3'-hydroxy-n-nonyl)-3-methyl-5-[4-(N-methoxycarbonylmethylamino)-n-butyl]hydantoin. (0.6 g, 61%) as a pale red oil.

I.R. (cm$^{-1}$) 3450 (OH); 3350 (NH); 1765, 1705 (hydantoin); 1740 (ester C=O).

N.M.R. ($\tau$)

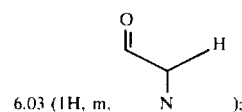

6.03 (1H, m, 6.27, 6.30 (3H, 2×s, OCH$_3$); 6.50, 6.62 (2H, 2×x, NCH$_2$C=O); 7.00 (3H, s, CH$_3$N);

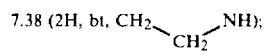

7.38 (2H, bt, CH$_2$–CH$_2$–NH);

7.80 (2H, b, OH, NH removed with D$_2$O); 9.13 (3H, b, terminal methyl group).

H.R.M.S. C$_{20}$H$_{37}$N$_3$O$_5$ requires 399.2733. Found 399.2743.

PHARMACOLOGICAL DATA

Bronchodilator activity

1. The compounds were examined for their ability to inhibit 5-hydroxytryptamine induced bronchoconstriction in the anaesthetised, artificially respired guinea pig (Konzett-Rossler preparation). The compounds were administered intravenously.

| Compound | ED$_{50}$/µg per kg |
|---|---|
| 1 | 2.3 |
| 2 | 32 |
| 3 | 108 |
| 5 | 95 |
| 6 | 79 |
| 9 | 66 |
| 10 | 80.5 |

2. The compounds were examined for their ability to protect conscious guinea pigs against bronchoconstriction induced by an histamine aerosol (Herxheimer test). In these experiments the compounds were administered by aerosol.

Compound 2 at 10 µg/ml gave a 47.5% increase in pre-convulsive coughing time 2 minutes after dosing.

Compound 3 at 10 µg/ml gave a 107% increase in preconvulsive coughing time 2 minutes after dosing.

Anti-Gastric Secretory Activity

The compounds were examined for their ability to inhibit pentagastrin-stimulated gastric acid secretion in the anaesthetised, perfused rat stomach preparation (Ghosh and Schild preparation, Parsons modification- M. Parsons PH.D. Thesis, Univ. of London, 1970). The Compounds were administered intravenously. The compound of Example 1 (g) was active at 0.4 mg/kg. The compound of Example 3 (compound 3) was active at 0.8 mg/kg.

Toxicity

No toxic effects were observed during the tests reported above.

We claim:

1. A compound of the formula:

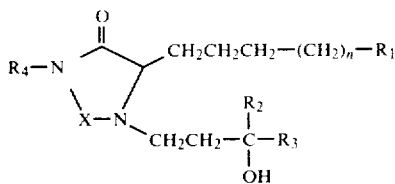

or a pharmaceutically acceptable salt thereof, wherein
n has a value of 0 to 5
R$_1$ is an aminomethyl function selected from the group consisting of
(a)

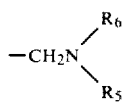

wherein each of R$_5$ and R$_6$ is independently hydrogen or alkyl of 1 to 6 carbon atoms;
(b)

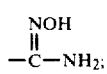

(c)

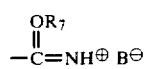

wherein R$_7$ is hydrogen or alkyl of 1 to 6 carbon atoms and B$^\ominus$ is a pharmaceutically acceptable anion; and
(d) —CH$_2$NHR$_8$ wherein R$_8$ is —SO$_2$R$_9'$, —COR$_9'$,

or —(CH$_2$)$_m$CO$_2$R$_9'$ in which
R$_9$ is hydrogen or alkyl of 1 to 6 carbon atoms,
R$_9'$ is alkyl of of 1 to 6 carbon atoms, benzyl or benzyl substituted with chloro, bromo, nitro or trifluoromethyl;
Z is oxygen or sulfur; and
m has a value of from 0 to 4;
R$_2$ is hydrogen or alkyl of 1 to 4 carbon atoms;
R$_3$ is alkyl of 1 to 9 carbon atoms, cycloalkyl of 5 to 8 carbon atoms, or alkyl of 1 to 6 carbon atoms substituted with cycloalkyl of 5 to 8 carbon atoms or
R$_2$ and R$_3$ together with the carbon atom to which they are attached are cycloalkylidene of 5 to 8 carbon atoms;
R$_4$ is hydrogen or alkyl of 1 to 6 carbon atoms; and
X is

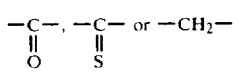

2. A compound according to claim 1 having the formula:

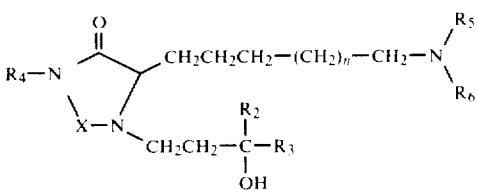

or a pharmaceutically acceptable salt thereof wherein
n has a value of 0 to 5;
R$_2$ is hydrogen or alkyl of 1 to 4 carbon atoms;
R$_3$ is alkyl of 1 to 9 carbon atoms, cycloalkyl of 5 to 8 carbon atoms or alkyl of 1 to 6 carbon atoms substituted by cycloalkyl of 5 to 8 carbon atoms, or
R$_2$ and R$_3$ together with the carbon atom to which they are attached are cycloalkylidene of 5 to 8 carbon atoms;
R$_4$ is hydrogen or alkyl of 1 to 6 carbon atoms;
each of R$_5$ and R$_6$ is hydrogen or alkyl of 1 to 6 carbon atoms; and
X is

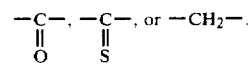

3. A compound according to claim 12 wherein
n is 2, 3 or 4 and
X is

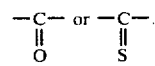

4. A compound according to claim 2 wherein R$_3$ is n-pentyl, n-hexyl or n-heptyl.

5. The compound according to claim 2 which is 1-(3-hydroxy-3-methylnonyl)-3-methyl-5-(7-aminoheptyl) hydantoin.

6. The compound according to claim 2 which is 1-(3-hydroxynonyl)-3-methyl-5-(4-aminobutyl) hydantoin.

7. A compound according to claim 1 having the formula:

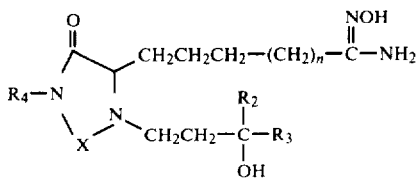

or a pharmaceutically acceptable salt thereof wherein
n has a value of 0 to 5;
R$_2$ is hydrogen or alkyl of 1 to 4 carbon atoms;
R$_3$ is alkyl of 1 to 9 carbon atoms, cycloalkyl of 5 to 8 carbon atoms or alkyl of 1 to 6 carbon atoms substituted by cycloalkyl of 5 to 8 carbon atoms, or
R$_2$ and R$_3$ together with the carbon atom to which they are attached are cycloalkylidene of 5 to 8 carbon atoms;
R$_4$ is hydrogen or alkyl of 1 to 6 carbon atoms;
each of R$_5$ and R$_6$ is hydrogen or alkyl of 1 to 6 carbon atoms; and
X is

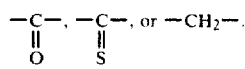

8. A compound according to claim 7 wherein
n is 2, 3 or 4 and
X is

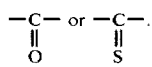

9. A compound according to claim 7 wherein $R_3$ is n-pentyl, n-hexyl or n-heptyl.

10. The compound according to claim 7 which is 1-(3-hydroxy-3-methylnonyl)-3-methyl-5-(6-amidoxylhexyl) hydantoin.

11. A compound according to claim 1 having the formula:

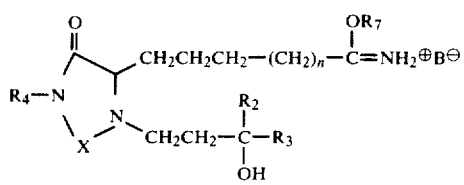

or a pharmaceutically acceptable salt thereof wherein
n has a value of 0 to 5;
$R_2$ is hydrogen or alkyl of 1 to 4 carbon atoms;
$R_3$ is alkyl of 1 to 9 carbon atoms, cycloalkyl of 5 to 8 carbon atoms or alkyl of 1 to 6 carbon atoms substituted by cycloalkyl of 5 to 8 carbon atoms, or
$R_2$ and $R_3$ together with the carbon atom to which they are attached are cycloalkylidene of 5 to 8 carbon atoms;
$R_4$ is hydrogen or alkyl of 1 to 6 carbon atoms;
each of $R_5$ and $R_6$ is hydrogen or alkyl of 1 to 6 carbon atoms;
$R_7$ is alkyl of 1 to 6 carbon atoms;
$B^\ominus$ is a pharmaceutically acceptable anion; and
X is

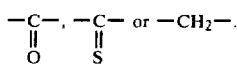

12. A compound according to claim 11 wherein
$R_7$ is methyl or ethyl and
$B^\ominus$ is a halide anion.

13. A compound according to claim 11 wherein
n is 2, 3 or 4 and
X is

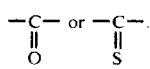

14. A compound according to claim 11 wherein $R_3$ is n-pentyl, n-hexyl or n-heptyl.

15. A compound according to claim 1 having the formula:

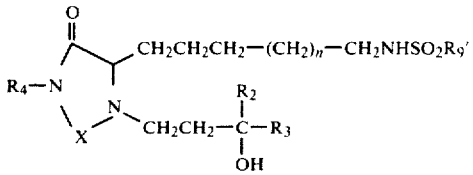

or a pharmaceutically acceptable salt thereof wherein
n has a value of 0 to 5;
$R_2$ is hydrogen or alkyl of 1 to 4 carbon atoms;
$R_3$ is alkyl of 1 to 9 carbon atoms, cycloalkyl of 5 to 8 carbon atoms or alkyl of 1 to 6 carbon atoms substituted by cycloalkyl of 5 to 8 carbon atoms, or
$R_2$ and $R_3$ together with the carbon atom to which they are attached are cycloalkylidene of 5 to 8 carbon atoms;
$R_4$ is hydrogen or alkyl of 1 to 6 carbon atoms; each of $R_5$ and $R_6$ is hydrogen or alkyl of 1 to 6 carbon atoms;
$R_9'$ is alkyl of 1 to 6 carbon atoms, benzyl or benzyl substituted with chloro, bromo, nitro or trifluoromethyl; and
X is

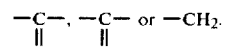

16. A compound according to claim 15 wherein
n is 2, 3 or 4 and
X is

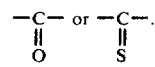

17. A compound according to claim 15 wherein $R_3$ is n-pentyl, n-hexyl or n-heptyl.

18. The compound according to claim 15 which is 1-(3-hydroxy-3-methylnonyl)-3-methyl-5-(7-methanesulfonamidoheptyl)hydantoin.

19. A compound according to claim 1 having the formula:

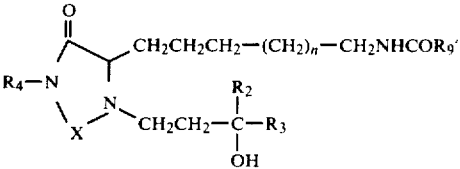

or a pharmaceutically acceptable salt thereof wherein
n has a value of 0 to 5;
$R_2$ is hydrogen or alkyl of 1 to 4 carbon atoms;
$R_3$ is alkyl of 1 to 9 carbon atoms, cycloalkyl of 5 to 8 carbon atoms or alkyl of 1 to 6 carbon atoms substituted by cycloalkyl of 5 to 8 carbon atoms, or
$R_2$ and $R_3$ together with the carbon atom to which they are attached are cycloalkylidene of 5 to 8 carbon atoms;
$R_4$ is hydrogen or alkyl of 1 to 6 carbon atoms;
each of $R_5$ and $R_6$ is hydrogen or alkyl of 1 to 6 carbon atoms;

$R_9'$ is alkyl of 1 to 6 carbon atoms, benzyl or substituted with chloro, bromo, nitro or trifluoromethyl; and X is

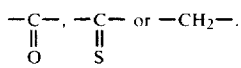

20. A compound according to claim 19 wherein n is 2, 3 or 4 and X is

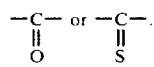

21. A compound according to claim 19 wherein $R_3$ is n-pentyl, n-hexyl or n-heptyl.

22. The compound according to claim 19 which is 1-(3-hydroxy-3-methylnonyl)-3-methyl-5-(7-acetamidoheptyl) hydantoin.

23. A compound according to claim 1 having the formula:

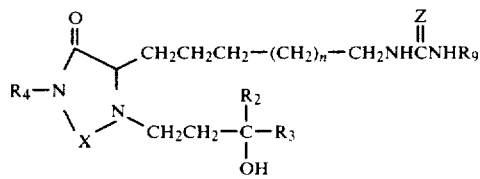

or a pharmaceutically acceptable salt thereof wherein
n has a value of 0 to 5;
$R_2$ is hydrogen or alkyl of 1 to 4 carbon atoms;
$R_3$ is alkyl of 1 to 9 carbon atoms, cycloalkyl of 5 to 8 carbon atoms; or alkyl of 1 to 6 carbon atoms substituted by cycloalkyl of 5 to 8 carbon atoms, or
$R_2$ and $R_3$ together with the carbon atom to which they are attached are cycloalkylidene of 5 to 8 carbon atoms;
$R_4$ is hydrogen or alkyl of 1 to 6 carbon atoms;
each of $R_5$ and $R_6$ is hydrogen or alkyl of 1 to 6 carbon atoms;
Z is oxygen or sulfur;
$R_9$ is hydrogen or alkyl of 1 to 6 carbon atoms; and
X is

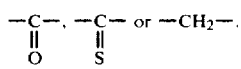

24. A compound according to claim 23 wherein n is 2, 3 or 4 and X is

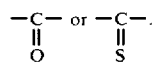

25. A compound according to claim 23 wherein $R_3$ is n-pentyl, n-hexyl or n-heptyl.

26. The compound according to claim 23 which is 1-(3-hydroxy-3-methylnonyl)-3-methyl-5-[7-(N-methylthiouriedo)heptyl]hydantoin.

27. A compound according to claim 1 having the formula:

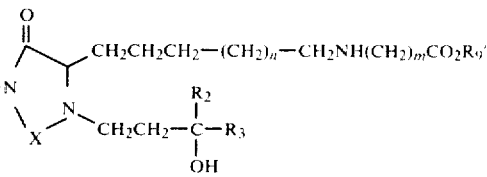

or a pharmaceutically acceptable salt thereof wherein
n has a value of 0 to 5;
$R_2$ is hydrogen or alkyl of 1 to 4 carbon atoms;
$R_3$ is alkyl of 1 to 9 carbon atoms, cycloalkyl of 5 to 8 carbon atoms or alkyl of 1 to 6 carbon atoms substituted by cycloalkyl of 5 to 8 carbon atoms, or
$R_2$ and $R_3$ together with the carbon atom to which they are attached are cycloalkylidene of 5 to 8 carbon atoms;
$R_4$ is hydrogen or alkyl of 1 to 6 carbon atoms;
each of $R_5$ and $R_6$ is hydrogen or alkyl of 1 to 6 carbon atoms;
$R_9'$ is alkyl of 1 to 6 carbon atoms, benzyl or benzyl substituted with chloro, bromo, nitro or trifluoromethyl;
X is

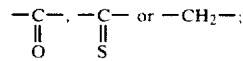

and
m has a value of 0 to 4.

28. A compound according to claim 27 wherein n is 2, 3 or 4 and X is

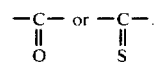

29. A compound according to claim 27 wherein $R_3$ is n-pentyl, n-hexyl or n-heptyl.

30. The compound according to claim 27 which is 1-(3-hydroxy-3-methylnonyl)-3-methyl-5-[7-(N-methoxycarbonylmethylamino)heptyl]hydantoin.

31. The compound according to claim 27 which is 1-(3-hydroxynonyl)-3-methyl-5-[4-carbobenzyloxyamino)butyl]hydantoin.

32. The compound according to claim 27 which is 1-(3-hydroxynonyl)-3-methyl-5-[4-(N-carbobenzyloxyamino)butyl]thiohydantoin.

33. A pharmaceutical composition comprising an amount of a compound according to claim 1 sufficient to effect a prostaglandin-like response in combination with a pharmaceutical carrier.

34. The method of effecting a prostaglandin-like response in a human or other animal which comprises administering thereto an effective amount of a compound according to claim 1.

* * * * *